US011318434B2

(12) United States Patent
Luciani et al.

(10) Patent No.: US 11,318,434 B2
(45) Date of Patent: May 3, 2022

(54) MULTILAYER CATALYTIC BED FOR THE PARTIAL OXIDATION OF N-BUTANE TO MALEIC ANHYDRIDE

(71) Applicant: POLYNT S.P.A., Scanzorosciate (IT)

(72) Inventors: Silvia Luciani, Colli del Tronto (IT); Federico Folco, Bergamo (IT); Mario Novelli, Seriate (IT); Stefano Gori, Bergamo (IT)

(73) Assignee: POLYNT S.P.A., Scanzorosciate (IT)

( * ) Notice: Subject to any disclaimer, the term of this patent is extended or adjusted under 35 U.S.C. 154(b) by 0 days.

(21) Appl. No.: 16/941,930

(22) Filed: Jul. 29, 2020

(65) Prior Publication Data
US 2021/0031160 A1 Feb. 4, 2021

(30) Foreign Application Priority Data

Jul. 29, 2019 (IT) .................. 102019000013167

(51) Int. Cl.
*B01J 8/00* (2006.01)
*B01J 23/18* (2006.01)
*B01J 23/30* (2006.01)
*B01J 27/18* (2006.01)
*C07D 307/60* (2006.01)

(52) U.S. Cl.
CPC .............. *B01J 8/008* (2013.01); *B01J 23/18* (2013.01); *B01J 23/30* (2013.01); *B01J 27/1802* (2013.01); *C07D 307/60* (2013.01)

(58) Field of Classification Search
CPC ... B01J 8/008; B01J 23/18; B01J 23/30; B01J 27/1802; B01J 27/1815; C07D 307/60

USPC .................................................. 502/209–213
See application file for complete search history.

(56) References Cited

U.S. PATENT DOCUMENTS 3,919,257 A * 11/1975 Milberger .............. B01J 27/186
549/260
4,075,232 A * 2/1978 Zagata ................. B01J 23/8876
549/260

(Continued)

FOREIGN PATENT DOCUMENTS

WO WO 00/72963 A1 12/2000

OTHER PUBLICATIONS

Italian Search Report dated Mar. 20, 2020 issued in IT 201900013167, together with partial translation.

(Continued)

*Primary Examiner* — Patricia L. Hailey
(74) *Attorney, Agent, or Firm* — Scully, Scott, Murphy & Presser, P.C.

(57) ABSTRACT

A catalytic bed for the partial oxidation of n-butane to maleic anhydride which comprises at least one first catalytic layer and at least one second catalytic layer, wherein each catalytic layer consists of a vanadium and phosphorus mixed oxide (VPO) catalyst and only the catalyst of the second catalytic layer further comprises tungsten, and wherein the second catalytic layer constitutes 25% to 45% of the total length of the catalytic bed and is arranged consecutively after the first catalytic layer along the direction in which the mixture of gases comprising the oxidation reagents flows. The present invention also relates to a process for producing maleic anhydride by partial oxidation of n-butane which uses the catalytic bed.

11 Claims, 4 Drawing Sheets

(56) References Cited

U.S. PATENT DOCUMENTS

| | | | | |
|---|---|---|---|---|
| 4,933,312 | A | * | 6/1990 | Haddad .................. B01J 23/002 502/209 |
| 5,137,860 | A | * | 8/1992 | Ebner .................... B01J 27/198 502/209 |
| 5,360,916 | A | | 11/1994 | Padia et al. |
| 5,364,824 | A | * | 11/1994 | Andrews ................ B01J 27/198 502/209 |
| 5,929,256 | A | * | 7/1999 | Felthouse .............. B01J 27/198 549/260 |
| 5,945,368 | A | | 8/1999 | Felthouse et al. |
| 6,194,587 | B1 | | 2/2001 | Doshi |
| 6,989,454 | B2 | * | 1/2006 | Hibst .................. C07D 307/60 549/262 |
| 2005/0256319 | A1 | * | 11/2005 | Weiguny .............. C07D 307/60 549/262 |
| 2007/0244332 | A1 | | 10/2007 | Padia et al. |
| 2013/0102455 | A1 | * | 4/2013 | Haddad ................ B01J 37/0201 502/8 |
| 2017/0014812 | A1 | * | 1/2017 | Haddad ................ B01J 35/0013 |

OTHER PUBLICATIONS

Pierini B.T. et al., "Cr, Mo and W used as VPO promoters in the partial oxidation of n-butane to maleic anhydride", Catalysis Today (Oct. 30, 2005), Elsevier, Amsterdam, NL, vol. 107-108, pp. 323-329.

Felthouse, Timothy R. et al., "Molybdenum-Promoted Vanadyl Pyrophosphate Catalysts for Reduction of Acrylic Acid During Selective Oxidation of Butane to Maleic Anhydride", (18th North American Catalysis Society Meeting Cancun, Mexico, Jun. 1-6, 2003).

Centi, G. et al., "Mechanistic Aspects of Maleic Anhydride Synthesis from C4 Hydrocarbons over Phosphorus Vanadium Oxide", Chem. Review (1988), vol. 88, pp. 55-80.

Arnold, III E.W. et al., "Effect of Water Vapor on the Activity and Selectivity Characteristics of a Vanadium Phosphate Catalyst towards Butane Oxidation", Applied Catalysis (1988), vol. 41, pp. 225-239.

Trifiro, F., "Key Properties of V-P Mixed Oxides in Selective Oxidation of C4 and C5 n-Paraffins", Catalysis Today (1993), vol. 16, pp. 91-98.

Volta, Jean-Claude, "Site isolation for light hydrocarbons oxidation", Topics in Catalysis (2001), vol. 15, pp. 121-129.

Chen, Bin et al., "Investigation of the Mechanism of n-Butane Oxidation on Vanadium Phosphorus Oxide Catalysts: Evidence from Isotopic Labeling Studies", J. Am. Chem. Soc. (2002), vol. 124, pp. 1638-1652.

Lorences, Maria J. et al., "Butane Oxidation to Maleic Anhydride: Kinetic Modeling and Byproducts", Ind. Eng. Chem. Res. (2003), vol. 42, pp. 6730-6742.

* cited by examiner

MULTILAYER CATALYTIC BED FOR THE PARTIAL OXIDATION OF N-BUTANE TO MALEIC ANHYDRIDE

The present invention relates to a catalytic bed for the partial oxidation of n-butane to maleic anhydride and to a process for the production of maleic anhydride that uses said catalytic bed.

Maleic anhydride is a well-known and versatile intermediate for the manufacture of unsaturated polyester resins, pharmaceutical products and agrochemical products. It is usually produced by partial catalytic oxidation of aromatic hydrocarbons (for example benzene) or non-aromatic hydrocarbons (for example n-butane).

The oxidation of non-aromatic hydrocarbons such as n-butane to maleic anhydride is performed in the gaseous phase, in the presence of a vanadium and phosphorus mixed oxide catalyst (so-called "VPO" catalyst) comprising vanadyl pyrophosphate $(VO)_2P_2O_7$ as main component. Furthermore, this catalyst may be modified by doping in order to comprise one or more promoter elements selected from groups IA, IB, IIA, IIB, IIIA, IIIB, IVA, IVB, VA, VB, VIA, VIB and VIIIA of the periodic table of elements.

Acrylic acid is a minor byproduct of the catalytic oxidation reaction of n-butane to maleic anhydride. With the current generation of VPO catalysts, during the production of maleic anhydride generally 1.5-1.8 kg of acrylic acid per 100 kg of supplied n-butane are formed. In industrial plants for the production of maleic anhydride, the entire downstream section, which consists for example of heat exchangers, condensers and distillation columns, is subject to soiling, which becomes apparent after long periods of activity during which polymers and/or oligomers of acrylic acid deposit, for example, in the distillation columns and obstruct the passage of the gases, thus decreasing the efficiency of the purification process.

In view of the above, there is the need to optimize the process for producing maleic anhydride so as to minimize or inhibit the formation of acrylic acid while maintaining the maleic anhydride yield unchanged.

Currently, the study of the reduction of acrylic acid formation during the oxidation reaction of n-butane to maleic anhydride has been the subject of a limited number of works of scientific literature. For example, Timothy R. Felthouse in *Molybdenum-Promoted Vanadyl Pyrophosphate Catalysts for Reduction of Acrylic Acid During Selective Oxidation of Butane to Maleic Anhydride* (18th North American Catalysis Society Meeting Cancun, Mexico, 1-6 Jun. 2003) shows the beneficial effect of molybdenum used as dopant of the VPO catalyst in order to mitigate the formation of acrylic acid at the expense, however, of the maleic anhydride yield.

Other authors have studied the reaction path that leads to the formation of acrylic acid, but the intermediates responsible for the formation of this compound have not been identified clearly and the steps that lead to the formation of acrylic acid have not been studied exhaustively, such that they are understood only partially or not at all. These works include those of Centi and Trifirò in Chem. Rev., 1988, 88, 88-50; Arnold E. W. in Applied Catalysis, 1988, 41, 225-239; Trifirò in Catalysis Today, 1993, 16, 91-98; Volta in Topics in Catalysis, 2001, 15, 121-129; Bin Chen and Eric J. Munson in J. Am. Chem. Soc., 2002, 124, 1638-1652; and Maria J. Lorences et al. in Ind. Eng. Chem. Res., 2003, 42, 6730-6742.

Patent literature describes some solutions for reducing the formation of acrylic acid, without however identifying a definitive manner for reducing selectively the acrylic acid yield without compromising the maleic anhydride yield or without altering the reaction conditions (such as for example promoting the conversion of n-butane to over-oxidize the acrylic acid to CO and $CO_2$). For example, in US Patent Application 2007/0244332 a lower selectivity in acrylic acid is obtained by feeding a trialkyl phosphate or a trialkyl phosphite together with the gaseous mixture of the reagents of the oxidation process. U.S. Pat. No. 5,945,368 instead describes the use of molybdenum as a promoter in a VPO catalytic system combined with a two-layer catalytic bed, in which however the maleic anhydride yield is not preserved. U.S. Pat. Nos. 5,360,916 and 6,194,587 describe a system in which the oxidation reaction of n-butane is performed in two distinct steps, by using two reactors in series in which the gaseous flow exiting from the first reactor is cooled by approximately 50° C. and then fed to the second reactor.

The aim of the present invention is therefore to provide a catalytic system for the partial oxidation of n-butane to maleic anhydride that allows to reduce the formation of acrylic acid without compromising the maleic anhydride yield.

Within the scope of this aim, an object of the invention is to provide a catalytic system for the partial oxidation of n-butane to maleic anhydride that reduces the formation of acrylic acid without the need to change the reaction conditions conventionally used in the industrial field.

This aim and these and other objects which will become better apparent hereinafter are achieved by a catalytic bed for the partial oxidation of n-butane to maleic anhydride comprising a first catalytic layer and a second catalytic layer, wherein the first catalytic layer and the second catalytic layer consist of a vanadium and phosphorus mixed oxide (VPO) catalyst comprising vanadyl pyrophosphate $(VO)_2P_2O_7$ as main component and only the VPO catalyst of the second catalytic layer further comprises tungsten, the second catalytic layer constitutes 25% to 45% of the total length of the catalytic bed and is arranged consecutively after the first catalytic layer, so that a mixture of gases comprising n-butane and oxygen flows first through the first catalytic layer and then through the second catalytic layer, and the VPO catalyst of the second catalytic layer comprises tungsten in an amount corresponding to an atomic ratio of vanadium to tungsten between 250:1 and 60:1.

The aim and objects of the present invention are furthermore achieved by a process for the production of maleic anhydride by partial oxidation of n-butane comprising the step of feeding into a reactor a gas mixture comprising n-butane and oxygen in the presence of the catalytic bed according to the invention.

Further characteristics and advantages of the invention will become better apparent from the following detailed description and from the accompanying drawings, wherein.

In a first aspect, the present invention relates to a catalytic bed for the partial oxidation of n-butane to maleic anhydride having the following characteristics:

(i) the catalytic bed comprises at least a first catalytic layer and a second catalytic layer, wherein each catalytic layer consists of a vanadium and phosphorus mixed oxide (VPO) catalyst comprising vanadyl pyrophosphate $(VO)_2P_2O_7$ as main component and only the VPO catalyst of the second catalytic layer further comprises tungsten as promoter element;

(ii) the second catalytic layer constitutes 25% to 45% of the total length of the catalytic bed and is arranged consecutively after the first catalytic layer along the direction in which the mixture of gases comprising n-butane and oxygen that is used to perform the oxidation of the n-butane to maleic anhydride flows, so that said mixture of gases flows first through the first catalytic layer and then through the second catalytic layer;

(iii) the VPO catalyst of the second catalytic layer comprises tungsten in an amount corresponding to an atomic ratio of vanadium to tungsten comprised between 250:1 and 60:1, preferably 100:1.

The inventors of the present invention have in fact observed that by using a catalytic bed having the characteristics described above it is possible to perform the partial oxidation of n-butane to maleic anhydride so as to reduce significantly the acrylic acid yield and at the same time keep the maleic anhydride yield substantially unchanged.

During the studies carried out by the inventors it has been observed that when the length of the second catalytic layer is about 36±5% of the total length of the catalytic bed, the maleic anhydride yield and the reduction in acrylic acid yield are maximized. Therefore, the second catalytic layer constitutes preferably 31% to 41%, and more preferably 36%, of the total length of the catalytic bed.

Although the catalytic bed of the present invention may comprise more than two catalytic layers, it may also consist only of the first and second catalytic layers, in which case the second catalytic layer constitutes 25%-45% of the total length of the catalytic bed and the first catalytic layer constitutes the remaining 75%-55% of the total length of the catalytic bed. When the catalytic bed consists only of the first and second catalytic layers, preferably the second catalytic layer constitutes 31%-41% of the total length of the catalytic bed and the first catalytic layer constitutes the remaining 69%-59% of the total length of the catalytic bed, and more preferably the second catalytic layer constitutes 36% of the total length of the catalytic bed and the first catalytic layer constitutes the remaining 64% of the total length of the catalytic bed.

The VPO catalyst of the first catalytic layer and/or the VPO catalyst of the second catalytic layer may further comprise, each independently of the other, at least one promoter element selected from the group consisting of magnesium, manganese, iron, cobalt, nickel, niobium, molybdenum, lanthanum, cerium, and bismuth, preferably bismuth.

In each one of the VPO catalysts, said promoter elements can be, independently of each other, in an amount corresponding to an atomic ratio of vanadium to promoter element comprised between 250:1 and 60:1, preferably 100:1.

In a preferred embodiment, the VPO catalyst of the second catalytic layer comprises tungsten in an amount corresponding to an atomic ratio of vanadium to tungsten of 100:1 and the second catalytic layer constitutes 36% of the length of the catalytic bed.

In another preferred embodiment, the catalytic bed consists of the first catalytic layer and the second catalytic layer, the second catalytic layer constitutes 25% to 45%, preferably 36%, of the total length of the catalytic bed, the VPO catalyst of the second catalytic layer comprises tungsten in an amount corresponding to an atomic ratio of vanadium to tungsten of 100:1, and the VPO catalyst of the first catalytic layer and the VPO catalyst of the second catalytic layer both comprise bismuth, preferably in an amount corresponding to an atomic ratio of vanadium to bismuth of 100:1.

In general, it has been observed that in VPO catalysts an atomic ratio of phosphorus to vanadium greater than 1 contributes to increase the activity of the vanadyl pyrophosphate and the selectivity to maleic anhydride. Therefore, in the catalytic bed of the present invention the VPO catalyst of the first catalytic layer and/or the VPO catalyst of the second catalytic layer may have, independently of each other, a phosphorus/vanadium atomic ratio between 1:1 and 1.8:1, preferably between 1.1:1 and 1.6:1.

The VPO catalysts used in the catalytic bed of the present invention can be prepared according to methods known to the person skilled in the art, in which a thermal treatment (so-called calcination) of a precursor of the catalyst represented by a vanadyl acid orthophosphate hemihydrate having formula $(VO)HPO_4 \cdot 0.5H_2O$ is performed.

The known methods for preparing said precursor (see for example U.S. Pat. No. 5,137,860 and EP 804963 A1) require conventionally the reduction of a pentavalent vanadium source (for example vanadium pentoxide $V_2O_5$) in conditions that lead the vanadium to a tetravalent state (average oxidation number +4) and the reaction of the tetravalent vanadium with a phosphorus source (for example orthophosphoric acid $H_3PO_4$). It is possible to use organic or inorganic compounds as reducing agents. Isobutyl alcohol is the most frequently used organic reducing agent, optionally mixed with benzyl alcohol.

By way of example, the precursor of each of the VPO catalysts used in the catalytic bed of the present invention can be prepared according to the method described in PCT publication WO 00/72963. In accordance with this method, the vanadium source and the phosphorus source react in the presence of an organic reducing agent which comprises (a) isobutyl alcohol, optionally mixed with benzyl alcohol, and (b) a polyol, in a weight ratio (a):(b) comprised between 99:1 and 5:95.

The precursor is then filtered, washed and optionally dried, preferably at a temperature between 120° C. and 200° C.

After its preparation as above, the precursor may be subjected to pelletization, granulation and tableting.

The transformation of the precursor into the active VPO catalyst (calcination) entails the conversion of the vanadyl acid orthophosphate hemihydrate of formula $(VO)HPO_4 \cdot 0.5H_2O$ of the precursor into the vanadyl pyrophosphate of formula $(VO)_2P_2O_7$ of the active VPO catalyst. This transformation comprises heating the precursor in the presence of nitrogen, preferably up to a calcination temperature of less than 600° C., and maintaining it at said calcination temperature. Substantially all the calcination methods described in the art can be used, including a method in which the thermal treatment of the precursor comprises the following steps:

(a) optional initial heating of the precursor in air up to an initial temperature of 250°–350° C.;

(b) optional holding of the initial temperature for 0.5-10 hours;

(c) heating of the precursor in nitrogen up to a calcination temperature of 500-600° C., and (d) holding at said calcination temperature for 0.5-10 hours.

After the transformation of the respective precursors into active VPO catalysts, these catalysts are ready to be used in a catalytic bed according to the present invention in order to perform the conversion of n-butane to maleic anhydride.

In a second aspect, the present invention relates to a process for the production of maleic anhydride by partial oxidation of n-butane, comprising the step of feeding into a reactor a mixture of gases comprising n-butane and oxygen in the presence of the catalytic bed of the present invention according to any one of the above embodiments.

The partial oxidation of the n-butane to maleic anhydride according to the process of the present invention can be performed at a temperature between 320° C. and 500° C.

The gas mixture that is fed to the reactor according to the process of the present invention can comprise n-butane at a concentration from 1.65 to 1.95 mol %.

As a function of the geometry of the VPO catalysts of the catalytic bed, the reactor used in the process of the present invention can be of the fixed-bed or fluid-bed type.

The invention will now be described with reference to the following non-limiting examples.

EXAMPLE 1—STUDY OF REACTION KINETICS

A study of the kinetics of the oxidation reaction of n-butane was carried out by means of catalytic tests performed with a commercial VPO catalyst "Polycat MAC4" (Polynt; Scanzorosciate, Italy), analyzing by gas chromatography and GC-MS the composition of the reaction products taken at different depths of the catalytic bed, and thus at different contact times.

Figure 1:
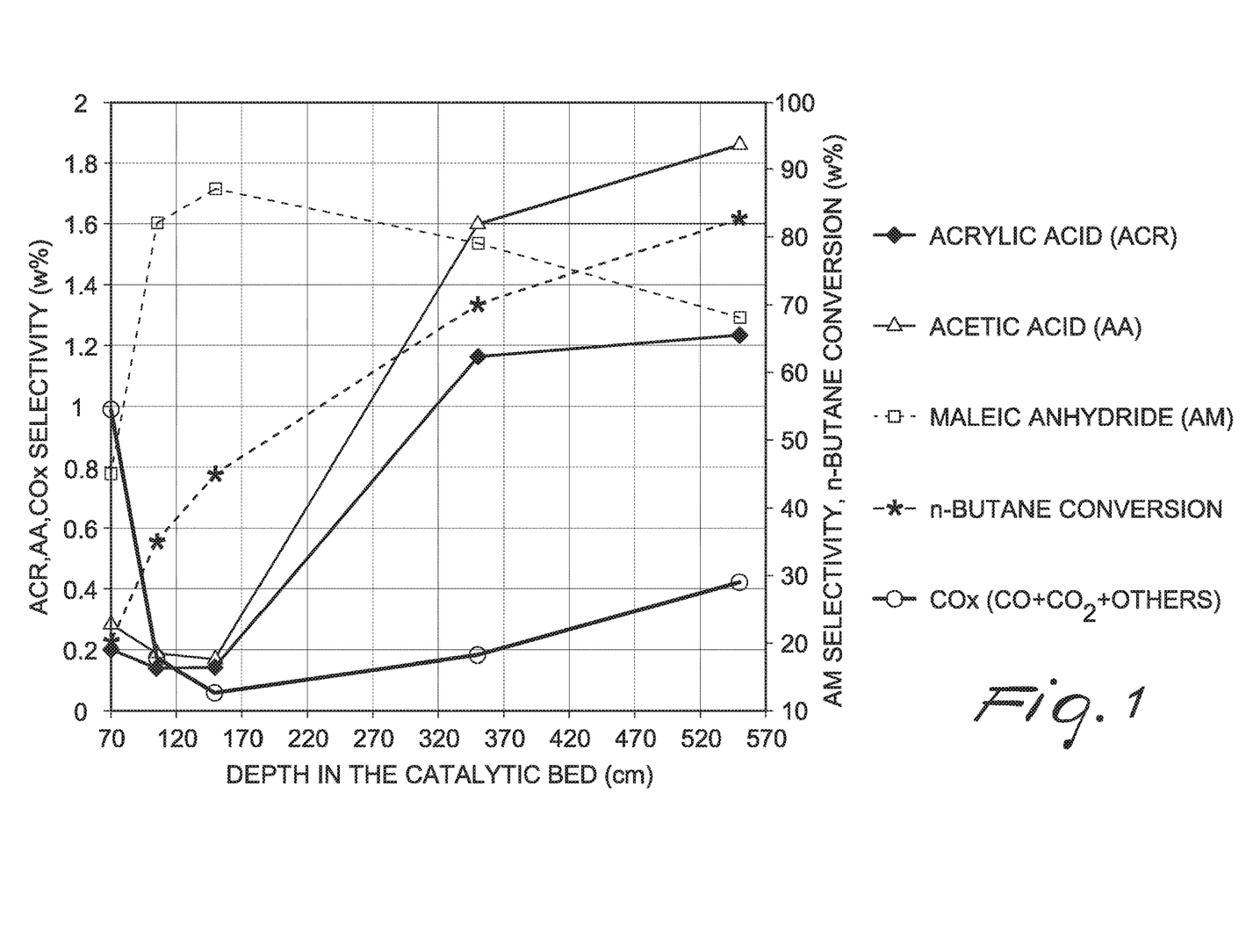
FIG. 1 is a chart illustrating the results of the study of the kinetics of the n-butane oxidation reaction performed in Example 1.

The result of the test is shown in graphic form in FIG. 1. It can be seen that the conversion of n-butane (Cony. C4) increases as a function of the depth of the catalytic bed, reaching approximately 20% at a depth of 70 cm, and then settles around 45% at approximately ⅓ of the depth of the catalytic bed. In this first part of the catalytic bed, selectivity to maleic anhydride (AM) increases up to a maximum of approximately 82%, while the selectivities of the byproducts such as acrylic acid (ACR) and acetic acid (AA) remain low, so that the formation of said byproducts is minimal and most of the oxidation intermediates are converted into maleic anhydride.

However, the finding that in the deepest part of the catalytic bed (between 350 cm and 550 cm) the selectivity in maleic anhydride decreases and the selectivities of acrylic acid, acetic acid and carbon oxides ($CO_x$) instead increase considerably, was completely unexpected. The maleic anhydride yield remains high because of the large increment of the conversion of n-butane, but in this portion of the catalytic bed the reaction becomes less selective and leads to a substantial increase in unwanted byproducts.

In view of the above, the inventors of the present invention have concluded that acrylic acid starts to form already halfway along the catalytic bed and that the greatest formation of this byproduct occurs particularly in the last 36±5% of the length of the catalytic bed. On the basis of this observation, the inventors have thus concluded that in industrial conditions acrylic acid is formed predominantly by means of consecutive oxidation reactions (decomposition) of maleic anhydride and only to a minor extent by means of non-selective parallel reactions of intermediates generated by n-butane.

Taking into consideration the reactivity of acrylic acid and the observation that this byproduct begins to form already halfway along the catalytic bed, the inventors of the present invention have therefore hypothesized the possibility of reducing the formation of acrylic acid by using in the last portion of the catalytic bed a VPO catalyst modified in a targeted manner. Different formulations of VPO catalyst were therefore prepared by adding one or more promoter elements, then studying their catalytic performance in terms of maleic anhydride yield and acrylic acid yield.

EXAMPLE 2—PREPARATION OF CATALYSTS

The following catalysts were prepared:
1) VPO catalyst promoted with bismuth (atomic ratio V/Bi 100:1);
2) VPO catalyst promoted with bismuth (atomic ratio V/Bi 100:1) and niobium (atomic ratio V/Nb 100:1);
3) VPO catalyst promoted with bismuth (atomic ratio V/Bi 100:1) and tungsten (atomic ratio V/W 100:1);
4) VPO catalyst promoted with bismuth (atomic ratio V/Bi 100:1) and boron (atomic ratio V/B 100:1).

The effect sought with catalysts 2 and 3 is the increase in activity, while with catalyst 4 it was sought to obtain a positive effect on the selectivity in maleic anhydride.

All the catalysts were prepared as described hereinafter, using the doping agents and their relative amounts shown in the following Table I in order to introduce the respective promoter elements in the catalysts.

TABLE I

| Catalyst | 1 | 2 | 3 | 4 |
|---|---|---|---|---|
| Doping agent I | Bismuth tris(2-ethylhexanoate) | | | |
| | 150.5 g | 150.5 g | 150.5 g | 150.5 g |
| Doping agent II | — | Niobium oxalate | Tungstic acid | Boric acid |
| | — | 50.9 g | 92.9 g | 12.5 g |

13.556 kg of isobutyl alcohol were placed in a 30 L reaction flask provided with a heating jacket and a reflux condenser and then 1.815 L of benzyl alcohol were added. Then bismuth tris(2-ethylhexanoate) (doping agent I) was added and, where foreseen, doping agent II was added.

Subsequently, 1883 g of vanadium pentoxide ($V_2O_5$) and 2846 g of phosphoric acid ($H_3PO_4$ 100%) were added to the solution. About 2 hours after the beginning of the loading operations, the head temperature of the condenser reached 80° C., the temperature at which the solvent starts to condense and reflux. From this moment the reaction continued for 16 hours, at the end of which a bright turquoise product was obtained.

The product thus obtained was then unloaded from the flask and filtered on a Buchner-type filter. The solid residue (cake) resulting from the filtration was placed in a tray and dried in an oven at 150° C. for one night. The process of removal of the carbon deriving from the reaction solvent was completed with a second thermal treatment in an oven at 260° C. Finally, 1762 g of precursor of VPO catalyst were obtained from 2412 g of filtrate. This precursor was subjected to a first step of pelletization and subsequent granulation and the resulting granulate was subjected to tableting, thus obtaining tablets having the shape of small perforated cylinders.

In order to convert the precursor into the VPO catalyst, the tablets of precursor were subjected to a thermal activation treatment performed in an oven, in flow, with a precise mixture of air/steam according to a temperature ramp that provides for:

a) initial heating of the precursor in air up to an initial temperature of 220° C. at a programmed rate of 390° C./h and holding in these conditions for 100 minutes;

b) heating of the precursor in a mixture of air (50% by volume) and steam (50% by volume) up to a calcination temperature of 420° C. at a programmed rate of 48° C./h and holding in these conditions for 430 minutes;

c) cooling from 420° C. to 290° C. with the same mixture of air and steam of step b) at a programmed rate of 94° C./h and subsequent cooling in only air from 290° C. to 100° C. at a programmed rate of 152° C./h.

EXAMPLE 3—CATALYTIC TESTS

The VPO catalysts prepared in Example 2 were subjected to catalytic tests in a single-tube pilot reactor. An amount of tablets of VPO catalyst was loaded in the reactor according to what is shown in the following Table II, so as to obtain a catalytic bed with a length of 3200 mm. The catalysts were then tested in the reaction conditions also shown in Table II.

TABLE II

| Catalyst | 1 | 2 | 3 | 4 |
|---|---|---|---|---|
| Loaded amount (g) | 831 | 876 | 845 | 825 |
| Air (Nl/h) | 2650 | 2650 | 2650 | 2650 |
| Gas hourly spatial velocity - GHSV ($h^{-1}$) | 2430 | 2430 | 2430 | 2430 |
| N-butane conc. (mol %) | 1.65 | 1.65 | 1.65 | 1.65 |
| Inlet pressure (kPa) | 140 | 140 | 140 | 140 |

The pilot reactor (hereinafter also catalyst tube or reaction tube) was submerged in a bath of liquid salts temperature-controlled by means of an electrical resistance heater, in order to convey the heat generated by the oxidation reaction of n-butane. The results of the catalytic tests are shown in the following Table III.

TABLE III

| Catalyst | 1 | 2 | 3 | 4 |
|---|---|---|---|---|
| T salts bath (° C.) | 404 | 404 | 404 | 404 |
| n-Butane conversion (%) | 82.5 | 82.5 | 81.5 | 82 |
| AM yield (% w) | 98.3 | 96 | 92.5 | 98.2 |
| AA yield (% w) | 1.53 | 1.20 | 0.40 | 1.64 |

In the reaction conditions used for the catalytic test, the catalyst 1 provided a maleic anhydride (AM) yield equal to approximately 98% by weight at a conversion of n-butane of 82.5%. The acrylic acid (AA) yield was 1.53% by weight, which corresponds to the values observed with commercial VPO catalysts of the background art. The catalyst 1 was therefore used as a reference sample.

By operating in reaction conditions analogous to those of the reference sample, catalyst 4 (comprising boron) provided yields of maleic anhydride and acrylic acid that are substantially equal to those of the reference sample. Therefore, the addition of boron as a promoter does not seem to have a direct effect on the reaction mechanism, neither on the first steps of activation of n-butane nor on the path of consecutive oxidation of maleic anhydride to acrylic acid.

Instead, the addition of niobium or tungsten has a clearly visible effect on the maleic anhydride yield. With catalyst 2 (comprising niobium), the maleic anhydride yield is 96% by weight, approximately 2% lower than the reference sample. With catalyst 3 (comprising tungsten) the maleic anhydride yield is instead 92.5% by weight, approximately 5% lower than the reference sample. A visible effect on the acrylic acid yield was also observed which, consistently with the greater activity of these catalysts, is lower than the reference sample. In a completely unexpected manner, catalyst 3 promoted with tungsten turned out to be by far more effective in the reduction of acrylic acid (0.40% by weight, equal to less than ⅓ of the value of 1.53% observed with the reference sample) than catalyst 2 promoted with niobium, which did not give rise to a particularly significant reduction of acrylic acid (1.20% by weight with respect to the value of 1.53% of the reference sample).

These catalytic tests have thus shown that the VPO catalyst comprising tungsten as promoter is the most active in selectively reducing the amount of acrylic acid, but that it is not capable of preserving the maleic anhydride yield. The inventors of the present invention have therefore decided to study the positive effect of the VPO catalyst comprising tungsten by using said catalyst only in the portion of catalytic bed where the kinetics study of Example 1 showed that the greatest formation of acrylic acid takes place.

EXAMPLE 4—TWO-LAYER CATALYTIC BED

Amounts of tablets of catalyst 1 and catalyst 3 of Example 2 according to what is shown in the following Table IV, were loaded into a single-tube pilot reactor, so as to obtain a two-layer catalytic bed having a total length of 3200 mm in which the layer of catalyst 3 is in the final part of the catalytic tube and the remaining part is occupied by the layer of catalyst 1.

Catalytic tests were performed on different compositions of the catalytic bed, obtained by varying the percentage in length of the catalytic bed occupied by the layer of catalyst 3 as shown in Table IV.

TABLE IV

| Bed composition | Loaded amount (g) | Layer length (mm) |
|---|---|---|
| Cat. 1 55% | 475 | 1760 |
| Cat. 3 45% | 396 | 1440 |
| Cat. 1 64% | 552 | 2048 |
| Cat. 3 36% | 328 | 1152 |
| Cat. 1 75% | 670 | 2400 |
| Cat. 3 25% | 205 | 800 |

For all the compositions of the two-layer catalytic bed shown in Table IV, the catalytic tests were performed using the following reaction conditions:
air=2650 Nl/h;
GHSV=2430 $h^{-1}$;
concentration of n-butane=1.65 mol %;
inlet pressure=140 kPa.

The results obtained are shown in the following Table V, which also includes as reference the results obtained in the test of Example 3 by using the two single-layer catalytic beds constituted respectively by catalyst 3 alone and by catalyst 1 alone.

TABLE V

| Bed composition | Temperature (° C.) | n-Butane conversion (%) | AM yield (% w) | AA yield (% w) |
|---|---|---|---|---|
| Cat. 1 0% Cat. 3 100% | 404 | 81.5 | 92.5 | 0.4 |

TABLE V-continued

| Bed composition | Temperature (° C.) | n-Butane conversion (%) | AM yield (% w) | AA yield (% w) |
|---|---|---|---|---|
| Cat. 1 55% Cat. 3 45% | 401 | 82.7 | 98.1 | 0.54 |
| Cat. 1 64% Cat. 3 36% | 404 | 81.9 | 98.8 | 0.44 |
| Cat. 1 75% Cat. 3 25% | 404 | 82.1 | 98 | 1.02 |
| Cat. 1 100% Cat. 3 0% | 404 | 82.5 | 98.3 | 1.53 |

Figure 2:
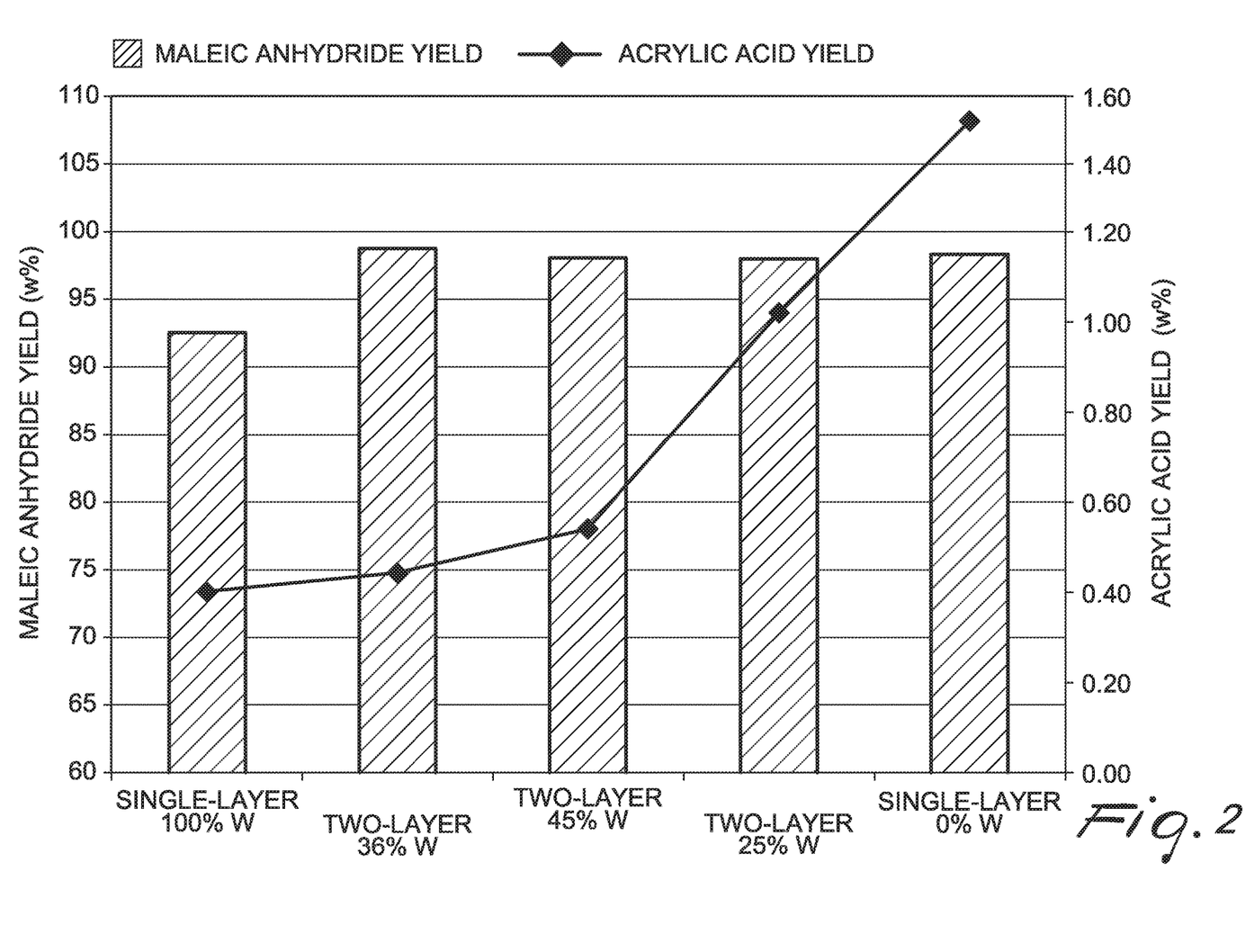
FIG. 2 is a chart illustrating the results of the catalytic tests performed in Example 4.

The results of Table V are summarized in graphic form in FIG. 2 and show that with respect to the values of the single-layer catalytic bed of catalyst 1 serving as reference (representative of the commercial catalytic systems of the current generation), the configuration with two layers of the catalytic bed of the present invention allows to selectively reduce the acrylic acid (AA) yield, while leaving the maleic anhydride (AM) yield substantially unchanged.

In particular, the two-layer catalytic bed of the present invention, in which the VPO catalyst layer comprising tungsten is equal to 25% of the total length of the bed, allows to obtain a reduction of the acrylic acid yield of approximately ⅓ with respect to the reference, passing from 1.53% by weight to 1.02% by weight, while the maleic anhydride yield remained at a value of approximately 98% by weight.

The best result was observed with the catalytic bed in which the layer of catalyst comprising tungsten is equal to 36% of the total length of the bed. In fact, the acrylic acid yield was reduced to 0.44% by weight and the maleic anhydride yield remained at approximately 98% by weight, therefore obtaining a reduction of the formation of acrylic acid comparable to that of the single-layer catalytic bed of catalyst 3 comprising tungsten, but without the disadvantageous reduction of maleic anhydride yield observed in that case.

EXAMPLE 5—IMPACT OF THE REACTION CONDITIONS

In order to verify whether the capacity of the catalytic bed of the present invention to reduce the formation of acrylic acid was stable over time and in different reaction conditions, a test lasting approximately 150 days was performed, during which first the reactor inlet pressure and then the concentration of the n-butane supplied were changed.

The test was performed with a catalytic bed having a total length of 3200 mm having the composition shown in Table VI and using the various reaction conditions also shown in Table VI.

TABLE VI

| Bed composition | Length (mm) | Air (Nl/h) | GHSV (h⁻¹) | Butane (mol %) | Inlet pressure (kPa) |
|---|---|---|---|---|---|
| Cat. 1 64% | 2048 | 2650 | 2430 | 1.65 | 140 |
|  |  |  |  | 1.75 | 155 |
| Cat 3 36% | 1152 |  |  | 1.85 | 165 |
|  |  |  |  | 1.95 |  |

Figure 3:
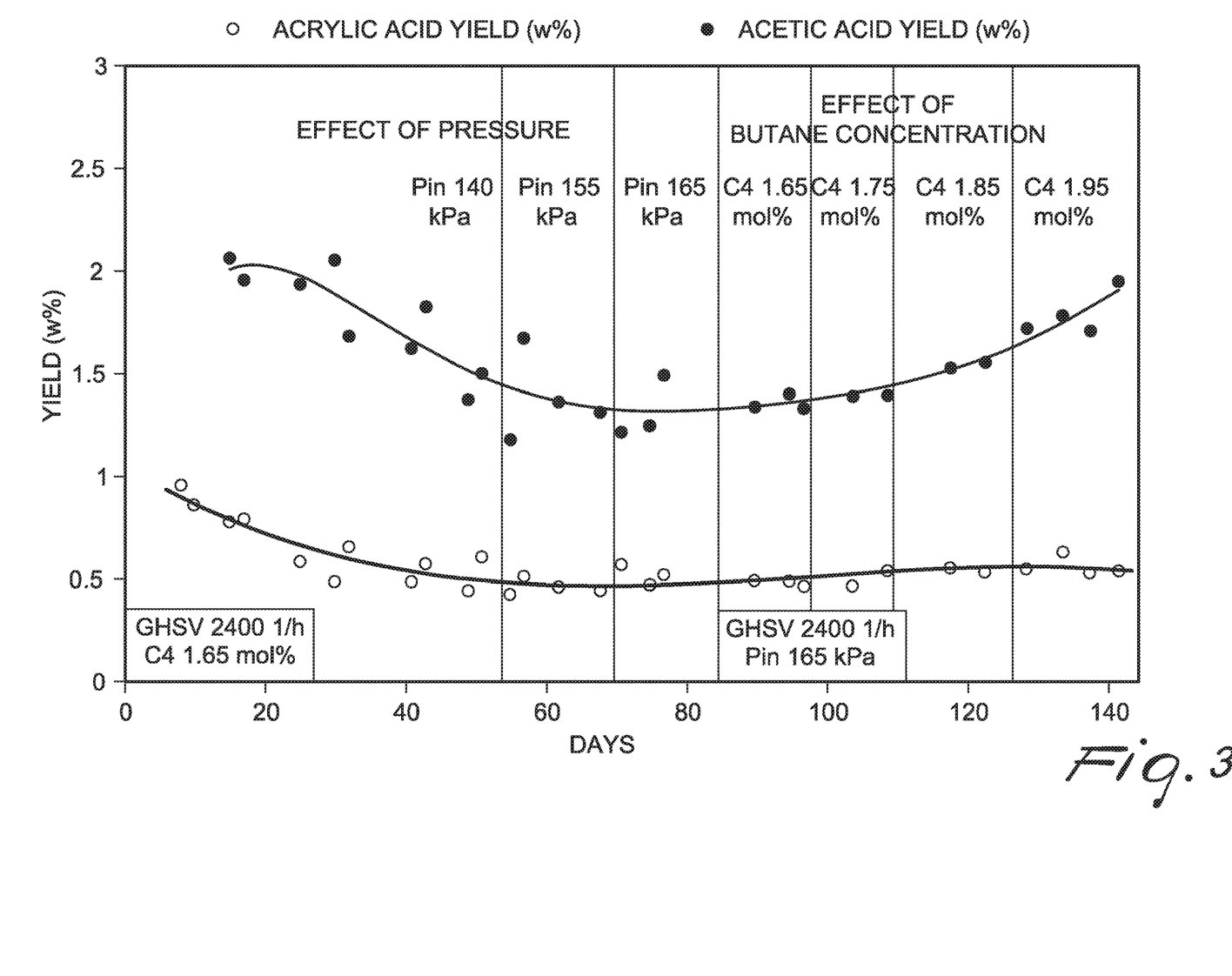
FIG. 3 is a chart illustrating the results of the catalytic tests performed in Example 5.

The result of the test is described in graphic form in FIG. 3. It is possible to notice that the two-layer catalytic bed of the present invention is not substantially affected by the variation of the concentration of n-butane in the mixture of gases being supplied nor by the variation of the inlet pressure. In particular, the acrylic acid yield remains substantially constant both in a wide range of concentrations of n-butane from 1.65 mol % up to 1.95 mol % and over the whole range of inlet pressures from 140 kPa to 165 kPa.

EXAMPLE 6—ROBUSTNESS TEST

A further test was performed in order to verify the robustness of the system based on the two-layer catalytic bed according to the present invention, using a reactor with a length of 6 meters (corresponding to a total length of the catalytic bed of 5500 mm).

This test was performed in two different operating conditions used in some industrial contexts (defined as "mild" and "stressing"), the characteristics of which are shown in the following Table VII.

TABLE VII

| Conditions | Air (Nl/h) | GHSV (h⁻¹) | Butane (mol %) | Inlet pressure (kPa) |
|---|---|---|---|---|
| mild | 3130 | 1675 | 1.80 | 180 |
| stressing | 3750 | 2000 | 2.00 | 200 |

Both a two-layer catalytic bed according to the invention and a single-layer catalytic bed were used, as shown in Table VIII.

TABLE VIII

| Catalytic bed | Composition | Length |
|---|---|---|
| Two-layer | Cat. 1 64% | 3520 mm |
|  | Cat. 3 36% | 1980 mm |
| Single-layer | Cat. 1 100% | 5500 mm |
|  | Cat. 3 0% | — |

Figure 4:
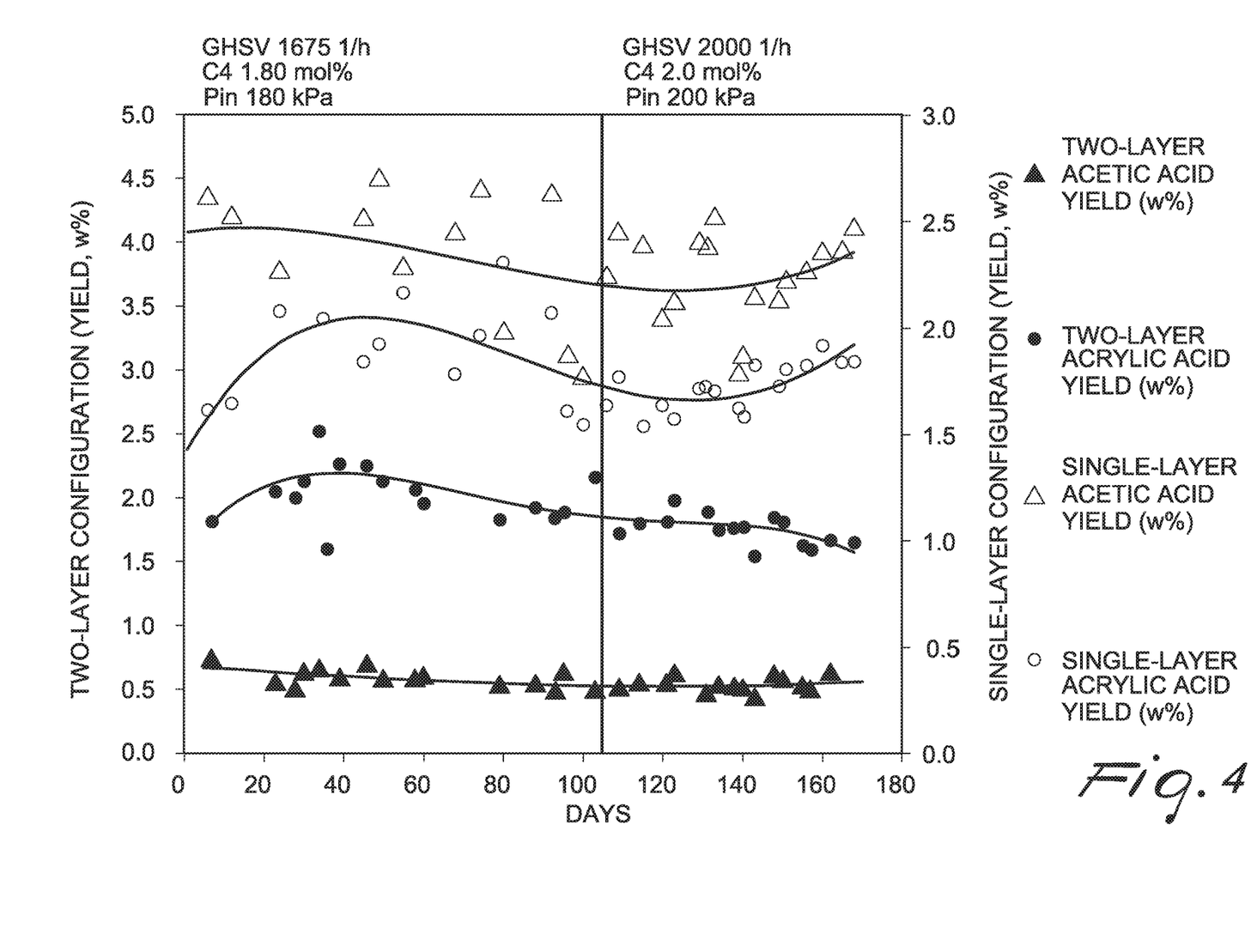
FIG. 4 is a chart illustrating the results of the catalytic tests performed in Example 6.

The result of the test is given in graphic form in FIG. 4, where the part on the left of the figure refers to the mild conditions and the part on the right refers to the stressing conditions. It may be noted that when using the same conditions, the two-layer catalytic bed of the present invention allows in any case to considerably reduce the acrylic acid yield for the entire duration of the test.

In practice it has been found that the catalytic bed according to the invention fully achieves the intended aim and objects, since it provides a catalytic system for the partial oxidation of n-butane to maleic anhydride in which the formation of acrylic acid is reduced substantially with respect to traditional catalytic systems, without affecting the maleic anhydride yield.

In this context, it has been observed also that the catalytic bed according to the invention achieves the intended aim without the need to alter the reaction conditions with respect to those conventionally used in the industrial field for the partial oxidation of n-butane to maleic anhydride.

The disclosures in Italian Patent Application No. 102019000013167 from which this application claims priority are incorporated herein by reference.

What is claimed is:

1. A catalytic bed for the partial oxidation of n-butane to maleic anhydride comprising a first catalytic layer and a second catalytic layer, wherein
   the first catalytic layer and the second catalytic layer consist of a vanadium and phosphorus mixed oxide (VPO) catalyst comprising vanadyl pyrophosphate (VO)$_2$P$_2$O$_7$ as main component and only the VPO catalyst of the second catalytic layer further comprises tungsten, the second catalytic layer constitutes 25% to 45% of the total length of the catalytic bed and is arranged consecutively after the first catalytic layer, so that a mixture of gases comprising n-butane and oxygen flows first through the first catalytic layer and then through the second catalytic layer, and the VPO catalyst of the second catalytic layer comprises tungsten in an amount corresponding to an atomic ratio of vanadium to tungsten between 250:1 and 60:1.

2. The catalytic bed according to claim 1, wherein the second catalytic layer constitutes 36% of the total length of the catalytic bed.

3. The catalytic bed according to claim 1, wherein the VPO catalyst of the second catalytic layer comprises tungsten in an amount corresponding to an atomic ratio of vanadium to tungsten of 100:1.

4. The catalytic bed according to claim 1, wherein the VPO catalyst of at least one of the first catalytic layer and the second catalytic layer further comprises at least one promoter element selected from the group consisting of magnesium, manganese, iron, cobalt, nickel, niobium, molybdenum, lanthanum, cerium, and bismuth.

5. The catalytic bed according to claim 4, wherein the at least one promoter element is bismuth.

6. The catalytic bed according to claim 1, wherein:
the catalytic bed consists of the first catalytic layer and the second catalytic layer;
the second catalytic layer constitutes 25% to 45% of the total length of the catalytic bed;
the VPO catalyst of the second catalytic layer comprises tungsten in an amount corresponding to an atomic ratio of vanadium to tungsten of 100:1; and
the VPO catalyst of the first catalytic layer and the VPO catalyst of the second catalytic layer further comprise bismuth.

7. The catalytic bed according to claim 6, wherein the second catalytic layer constitutes 36% of the total length of the catalytic bed.

8. The catalytic bed according to claim 1, wherein the VPO catalyst of the first catalytic layer and the VPO catalyst of the second catalytic layer have, independently of each other, a phosphorus/vanadium atomic ratio between 1:1 and 1.8:1.

9. The catalytic bed according to claim 8, wherein the VPO catalyst of the first catalytic layer and the VPO catalyst of the second catalytic layer have, independently of each other, a phosphorus/vanadium atomic ratio between 1.1:1 and 1.6:1.

10. A process for the production of maleic anhydride by partial oxidation of n-butane, comprising the step of feeding in a reactor a mixture of gases comprising n-butane and oxygen in the presence of a catalytic bed according to claim 1.

11. The process according to claim 10, wherein the mixture of gases comprises n-butane at a concentration from 1.65 to 1.95 mol %.

* * * * *